(12) United States Patent
Foerster

(10) Patent No.: US 6,585,730 B1
(45) Date of Patent: Jul. 1, 2003

(54) METHOD AND APPARATUS FOR ATTACHING CONNECTIVE TISSUES TO BONE USING A KNOTLESS SUTURE ANCHORING DEVICE

(75) Inventor: Seth A. Foerster, San Clemente, CA (US)

(73) Assignee: Opus Medical, Inc., San Juan Capistrano, CA (US)

( * ) Notice: Subject to any disclaimer, the term of this patent is extended or adjusted under 35 U.S.C. 154(b) by 265 days.

(21) Appl. No.: 09/651,253

(22) Filed: Aug. 30, 2000

(51) Int. Cl.$^7$ ............................................. A61B 17/04
(52) U.S. Cl. ......................................... 606/32; 411/80
(58) Field of Search ........................... 606/232, 72, 73; 411/80, 355, 511

(56) References Cited

U.S. PATENT DOCUMENTS

| | | |
|---|---|---|
| 3,143,916 A | 8/1964 | Rice |
| 4,301,551 A | 11/1981 | Dore et al. |
| 4,467,478 A | 8/1984 | Jurgutis |
| 4,483,023 A | 11/1984 | Hoffman, Jr. et al. |
| 4,590,928 A | 5/1986 | Hunt et al. |
| 4,597,776 A | 7/1986 | Ullman et al. |
| 4,605,414 A | 8/1986 | Czajka |
| 4,672,957 A | 6/1987 | Hourahane |
| 4,712,542 A | 12/1987 | Daniel et al. |
| 4,772,286 A | 9/1988 | Goble et al. |
| 4,823,780 A | 4/1989 | Odensten et al. |
| 5,195,542 A | 3/1993 | Gazielly et al. |
| RE34,293 E | 6/1993 | Goble et al. |
| 5,275,176 A | 1/1994 | Chandler |
| 5,324,308 A | 6/1994 | Pierce |
| 5,330,468 A | 7/1994 | Burkhart |
| 5,383,905 A | 1/1995 | Golds et al. |
| 5,441,508 A | 8/1995 | Gazielly et al. |
| 5,486,197 A * | 1/1996 | Le et al. ..................... 606/232 |
| 5,501,695 A | 3/1996 | Anspach, Jr. et al. |
| 5,545,180 A * | 8/1996 | Le et al. ..................... 606/232 |
| 5,549,617 A | 8/1996 | Green et al. |
| 5,562,689 A | 10/1996 | Green et al. |
| 5,573,548 A | 11/1996 | Nazre et al. |
| 5,575,801 A | 11/1996 | Habermeyer et al. |
| 5,584,835 A | 12/1996 | Greenfield |
| 5,584,839 A | 12/1996 | Gieringer |
| 5,591,207 A | 1/1997 | Coleman |
| 5,632,748 A * | 5/1997 | Beck, Jr. et al. .......... 606/72 X |
| D385,352 S | 10/1997 | Bales et al. |
| 5,681,333 A | 10/1997 | Burkhart et al. |
| 5,690,649 A | 11/1997 | Li |
| 5,697,950 A | 12/1997 | Fucci et al. |
| 5,702,397 A | 12/1997 | Goble et al. |
| 5,707,394 A | 1/1998 | Miller et al. |
| 5,782,865 A | 7/1998 | Grotz |
| 5,797,963 A | 8/1998 | McDevitt |

(List continued on next page.)

FOREIGN PATENT DOCUMENTS

FR  2 777 447  10/1999

OTHER PUBLICATIONS

PCT Search Report, Dec. 19, 2001.

Primary Examiner—Peter Nerbun
(74) Attorney, Agent, or Firm—Stout, Uxa, Buyan & Mullins, LLP; Donald E. Stout

(57) ABSTRACT

An innovative bone anchor and methods for securing connective tissue, such as tendons, to bone, which permit a suture attachment that ties entirely beneath the cortical bone surface. Advantageously, the suturing material between the connective tissue and the bone anchor is secured without the need for tying a knot. The suture attachment to the bone anchor involves the looping of a length of suturing material around a self-locking wedge block in the anchor, thereby avoiding an eyelet connection which requires a knot and which concentrates stress on a very small portion of the suturing material. Thus, failure rates are greatly decreased over conventional techniques, and the innovative procedures are significantly easier to perform than conventional techniques.

36 Claims, 15 Drawing Sheets

U.S. PATENT DOCUMENTS

| | | |
|---|---|---|
| 5,810,854 A | 9/1998 | Beach |
| 5,860,978 A | 1/1999 | McDevitt |
| 5,868,789 A | 2/1999 | Huebner |
| 5,879,372 A | 3/1999 | Bartlett |
| 5,893,850 A | 4/1999 | Cachia |
| 5,911,721 A | 6/1999 | Nicholson et al. |
| 5,935,129 A | 8/1999 | McDevitt et al. |
| 6,007,567 A | 12/1999 | Bonutti |
| 6,013,083 A | 1/2000 | Bennett |
| 6,022,373 A | 2/2000 | Li |
| 6,102,934 A | 8/2000 | Li .............. 606/232 |
| 6,146,406 A | 11/2000 | Shluzas et al. ......... 606/232 |
| 6,319,271 B1 * | 11/2001 | Schwartz et al. ......... 606/232 |
| 6,328,758 B1 | 12/2001 | Tornier et al. ............. 606/232 |
| 6,355,053 B1 | 3/2002 | Li .............. 606/232 |

* cited by examiner

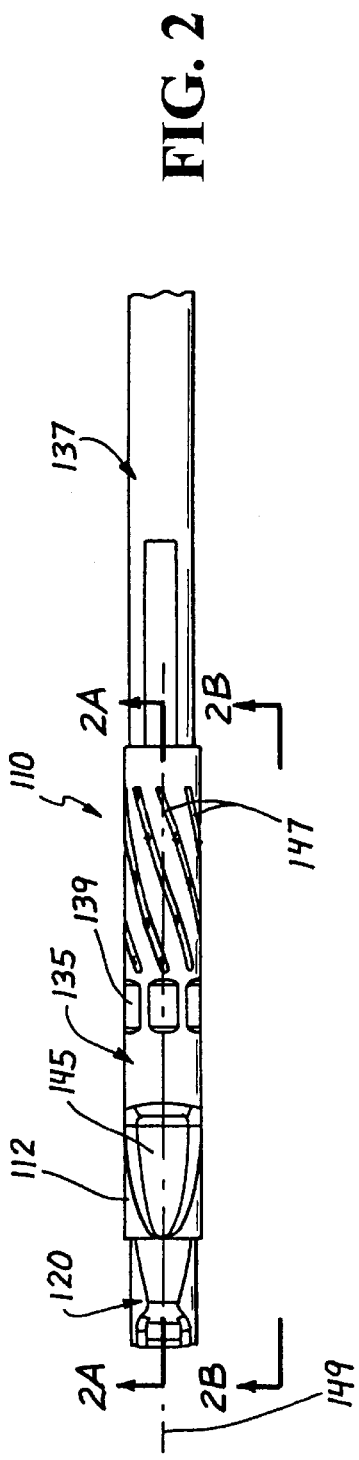
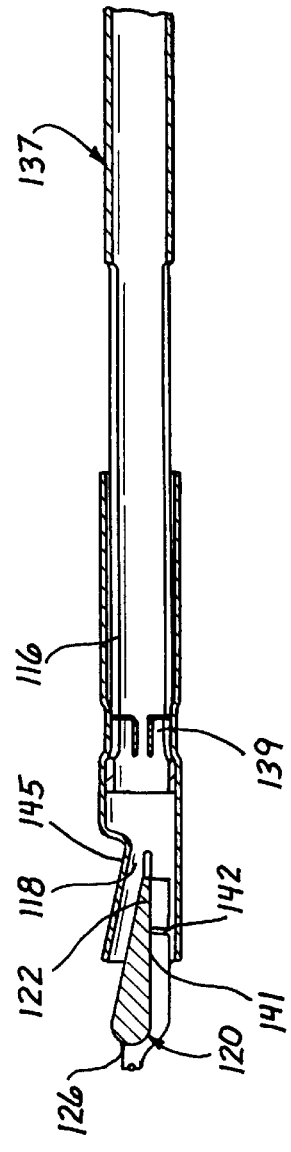
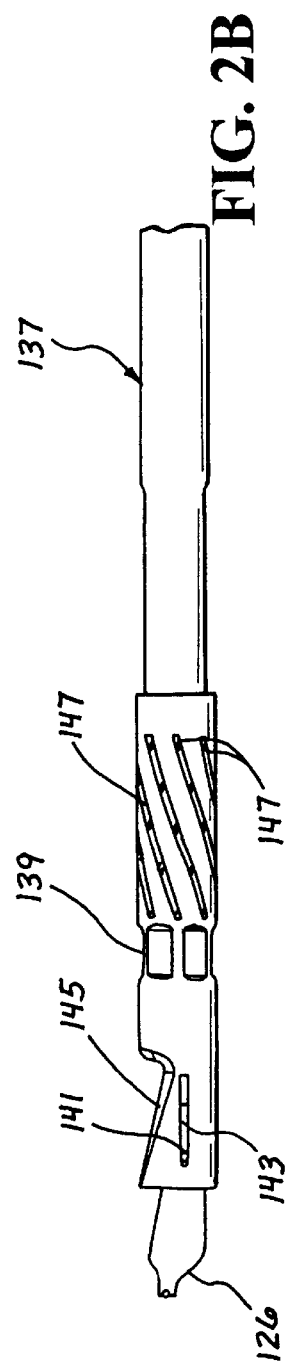
FIG. 2
FIG. 2A
FIG. 2B

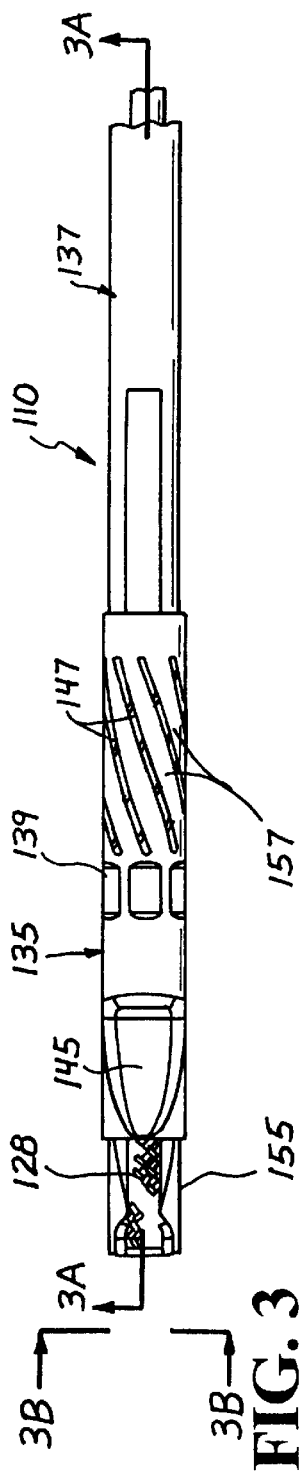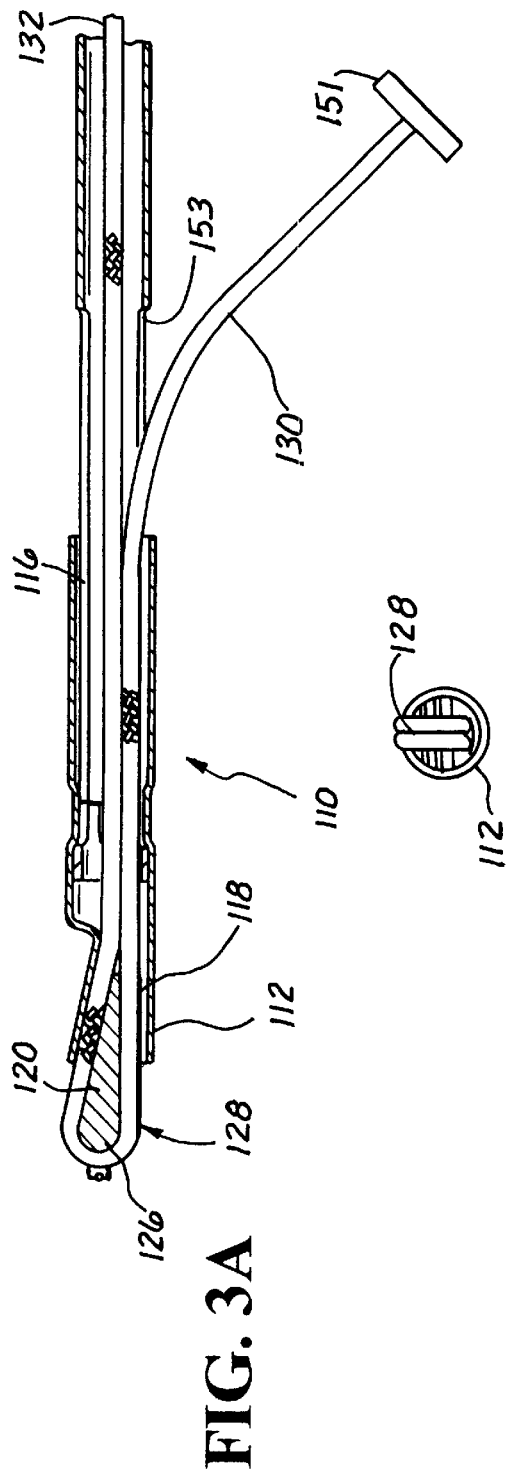
FIG. 3
FIG. 3A
FIG. 3B

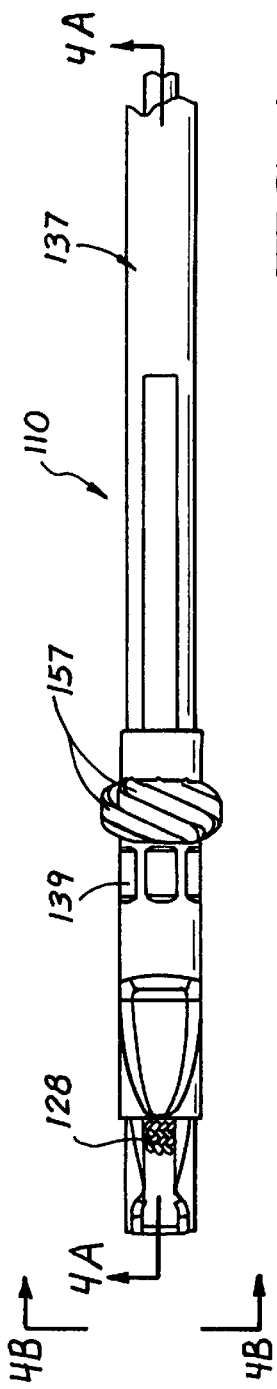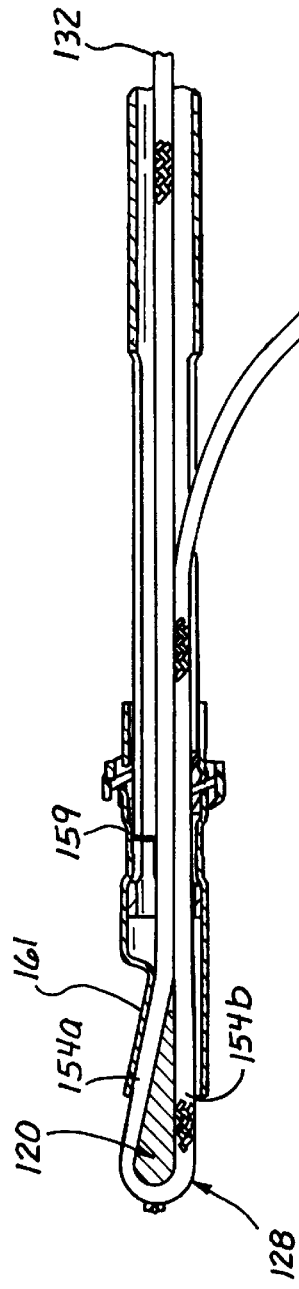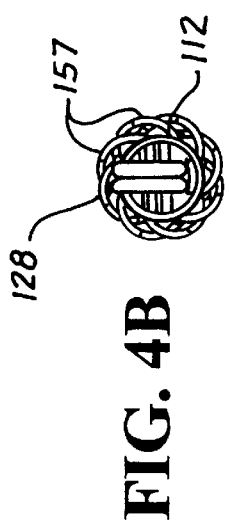
FIG. 4
FIG. 4A
FIG. 4B

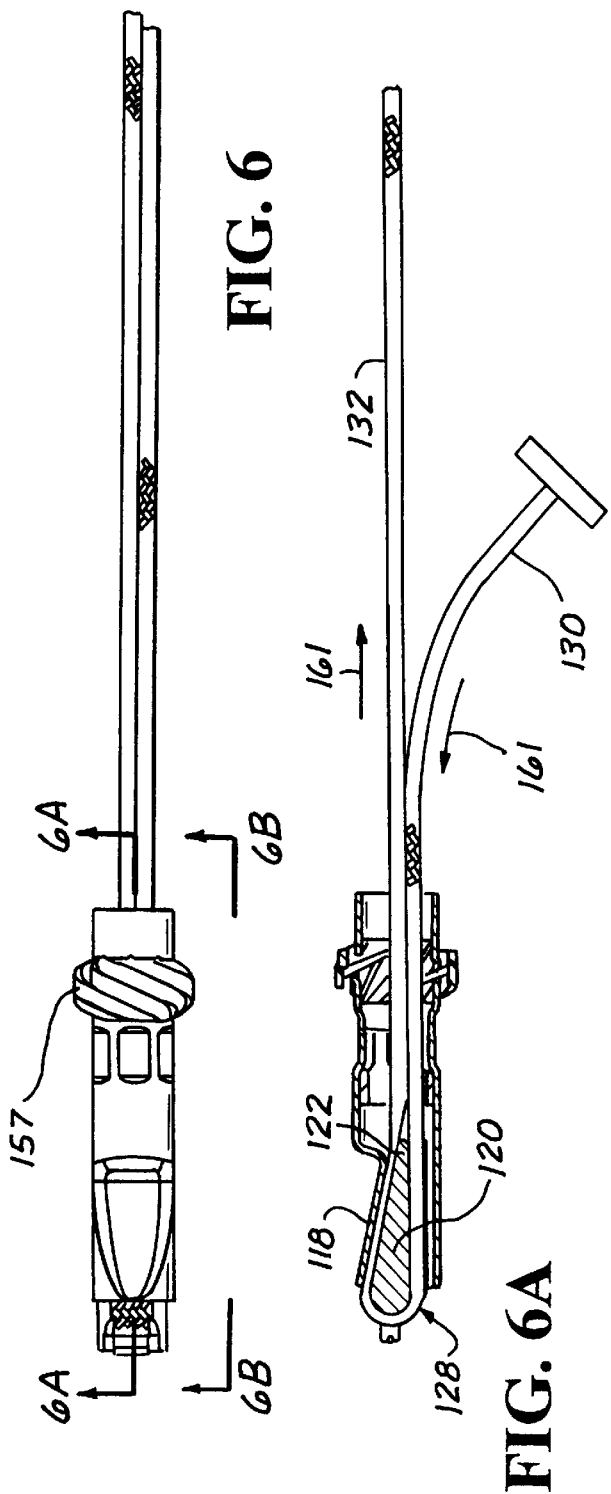
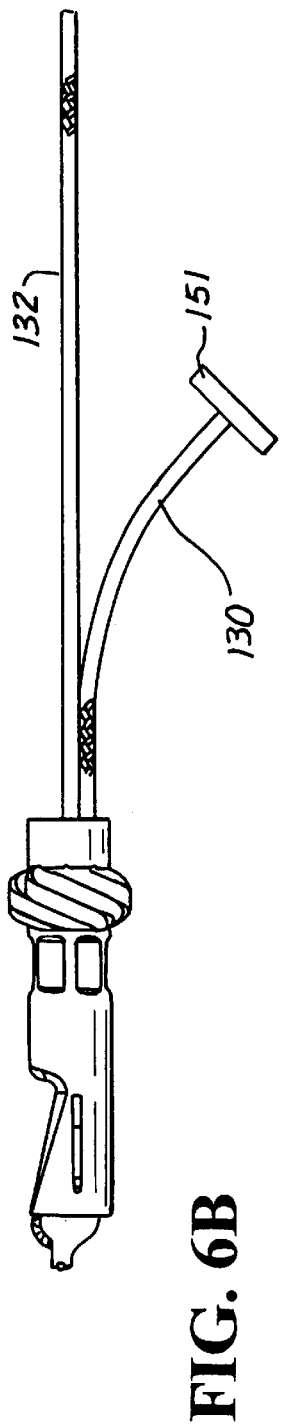
FIG. 6
FIG. 6A
FIG. 6B

METHOD AND APPARATUS FOR ATTACHING CONNECTIVE TISSUES TO BONE USING A KNOTLESS SUTURE ANCHORING DEVICE

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it is able to be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures are of the arthroscopic type, and are considered investigational in nature.

Another significant difficulty with current arthroscopic rotator cuff repair techniques are shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, breaking the sutures.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock-the ball into the race. Although this embodiment purports to be a self-locking anchor adapted for use in blind holes for fixing sutures into bone, the construct shown is complicated, and does not appear to be adequate to reliably fixate the suture.

What is needed, therefore, is a new approach for repairing the rotator cuff or fixing other soft tissues to bone, wherein suture tension can be adjusted and possibly measured, the suture resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention solves the problems outlined above by providing innovative bone anchor and connective techniques which permit a suture attachment which lies entirely beneath the cortical bone surface. In the present state of the art, the sutures which are passed through the tissues to be attached to bone typically are threaded through a small eyelet incorporated-into the head of the anchor and then secured by tying knots in the sutures. Endoscopic knot tying is an arduous and technically demanding task. Therefore, the present invention discloses devices and methods for securing sutures to a bone anchor without the requirement of knot tying.

In one embodiment, the suture legs, after having been placed into soft tissues to be anchored to bone, are threaded through the anchor and then through a floating wedge block located at the distal end of the anchor. The wedge block is configured such that it has a hollow lumen through the center, and a conically tapered outer surface. The distal end of the wedge block is the wider end of the cone, and the transition from the inside diameter created by the hollow lumen and the outside diameter created by the conical surface includes smooth radii for dressing the sutures threaded through the hollow lumen. The sutures are passed back around the outside of the wedge block such that they rest on the conical surface. They are then re-threaded in the opposite direction back through the anchor, exiting the anchor at the proximal end thereof. The anchor is then inserted into the bone, and secured. The distal end of the anchor is tapered to match the taper of the conical surface on the wedge block. When tension is placed on the legs of the suture passing back out of the anchor, the suture is drawn through the hollow center lumen, around the distal end of the wedge block, and back out of the anchor. This tension tends to cause the wedge block to force its way back up into the anchor body, and a means to prevent this may be employed. Such means may include any structure that selectively holds the wedge block separate from the anchor body.

At this juncture, by pulling on the suture legs, any slack in the sutures is removed, and the soft tissues are drawn toward the anchor. When the soft tissues are in the desired orientation, relative to the bone to which they are to be attached, the structure holding the wedge block is removed, and the back tension on the sutures pulls the wedge block into the matching taper in the anchor body, maintaining the compressive force on the suture legs.

In another embodiment, the wedge block may be adapted to have a U-shaped channel along one side of the wedge, and a tapered face along the opposite side of the wedge. The U-shaped channel communicates with the tapered face via a large radius surface that transitions and blends the channel face to the tapered face. The wedge is configured such that it may be placed inside of a hollow cylinder with a tapered face that protrudes into the interior of the cylinder and is configured to mate with the taper of the wedge. The wedge is adapted to permit two legs of the suture to be threaded through the anchor body, and along the U-shaped channel to the distal end of the anchor, wherein the sutures are drawn around the radiused surface and onto the tapered surface of the wedge on the opposite side. The sutures then pass back out of the proximal end of the anchor. As before, the suture legs may pass freely around the tapered wedge block until such time as tension in the bound legs pulls the wedge block back up into the tapered body of the anchor, and locks the suture in place.

Thus, with the above-described suture locking system, suture failure rates are dramatically reduced over conventional techniques because of the increased radius over which the suture is loaded, and the inventive procedures are significantly easier to perform than conventional techniques because of the elimination of knot tying.

More particularly, there is provided a bone anchor device for attaching connective tissue to bone, which comprises an outer body, and a lumen extending axially through the outer body. Inner walls which define the lumen in a proximal portion of the outer body extend inwardly relative to inner walls which define the lumen in a portion of the outer body distal to the proximal portion. A wedge member is advantageously disposed in a distal end of the lumen, distal to the inwardly extending lumen wall portion, which has outer walls that taper inwardly in a proximal direction therealong. The wedge member is axially movable in the lumen distal end.

In one preferred embodiment, a lumen extends axially through the wedge member, for receiving a suture therein. The wedge member preferably comprises a distal end having a curved surface, and the tapered proximal surface of the wedge member and the inwardly extending lumen internal wall together define a tapered distal lumen which communicates with the lumen.

A suture extends through the lumen and around the distal curved surface of the wedge member, and includes a free end extending proximally out of the bone anchor device and a bound end attached to soft tissue to be secured to the bone, wherein when the free end is placed in tension by a proximally directed force, the suture travels about the wedge member until increased tension on the bound end causes the suture to move the wedge member axially in a proximal direction, the proximal axial travel of the wedge member continuing until the proximal surface of the wedge member has moved into sufficient proximity to the inwardly extending internal lumen wall to pinch a length of the suture in the tapered distal lumen.

In another aspect of the invention, there is provided a bone anchor device for attaching connective tissue to bone, which comprises an outer body and a lumen extending axially through the outer body. Inner walls which define the lumen taper in a proximal portion of the outer body extend inwardly relative to inner walls which define the lumen in a portion of the outer body distal to the proximal portion. A suture clamping member, consisting of a wedge member, is axially movable in the lumen.

In still another aspect of the invention, there is provided a bone anchor device for attaching connective tissue to bone, which comprises an outer body having a lumen extending axially therethrough. Inner walls which define the lumen in a proximal portion of the outer body extend inwardly relative to inner walls which define the lumen in a portion of the outer body distal to the proximal portion. A suture clamping member comprising a wedge member is axially movable in the lumen distal portion. A suture extends through the lumen and around a distal surface of the wedge member, which includes a free end extending proximally out of the bone anchor device and a bound end attached to soft tissue to be secured to the bone. When the free end is placed in tension by a proximally directed force, the suture travels about the wedge member until increased tension on the bound end causes the suture to move the wedge member axially in a proximal direction, the proximal axial travel of the wedge member continuing until the proximal surface of the wedge member has moved into sufficient proximity to the inwardly extending internal lumen wall to pinch a length of the suture therebetween.

In another aspect of the invention, there is provided a bone anchor device for attaching connective tissue to bone, which comprises an outer body having an open distal end, and a lumen extending axially through the outer body. Inner walls which define the lumen in a proximal portion of the outer body extend inwardly relative to inner walls which define the lumen in a portion of the outer body distal to the proximal portion. A suture clamping member having an outer surface is disposed in the lumen distal end and is axially movable therein. Advantageously, complementary engaging structure is disposed on each of the suture clamping member outer surface and the lumen inner surface for retaining the suture clamping member in the lumen distal end when the bone anchor device is not in a portion of bone. This complementary engaging structure preferably comprises a pin disposed on one of the suture clamping member outer surface and the lumen inner surface, and a recess for receiving the pin disposed on the other of the suture clamping member outer surface and the lumen inner surface.

In yet another aspect of the invention, there is provided a bone anchor device for attaching connective tissue to bone, which.comprises an outer body having an outer surface, and a lumen extending axially through the outer body. Inner walls which define the lumen in a proximal portion of the outer body extend inwardly relative to inner walls which define the lumen in a portion of the outer body distal to the proximal portion. A suture clamping member is disposed in the lumen distal portion and is axially movable therein. Additionally, at least one outwardly extendable rib is disposed on the outer body outer surface for anchoring the outer body into surrounding bone.

In still another aspect of the invention, there is provided a bone anchor device for attaching connective tissue to bone, which comprises a distal wedge anchor portion comprising an outer body having an outer surface, on which a outwardly deployable anchoring element is situated. Additionally, a proximal driver portion is connected to the distal wedge anchor portion at a proximal end thereof, which includes an actuator for deploying the anchoring element outwardly. Advantageously, the connection between the proximal driver portion and the distal wedge anchor portion is releasable once the anchoring element has been deployed. In a preferred embodiment, this is accomplished because of a designed failure point in the connection between the proximal driver portion and the distal wedge anchor portion, so that upon deployment of the anchoring element outwardly, additional force may be applied to separate the driver portion from the anchor portion so that only the driver portion may be proximally removed from the patient's body.

In yet another aspect of the invention, there is disclosed a method for securing connective tissue to bone, which comprises securing a first end of a length of suture to a portion of soft tissue to be attached to a portion of bone. A second end of the length of suture is threaded through a lumen in an outer body of a bone anchor device and about an axially movable suture clamping member disposed in a distal portion of the lumen. The outer body is placed in a blind hole disposed in the portion of bone, and the second end of the length of suture is pulled proximally, so that the suture travels about the axially movable suture clamping member and draws the first end of the length of suture toward the bone anchor device, thereby securing the portion of soft tissue snugly to the portion of bone. Advantageously, when the tension on the first end of the length of suture increases, as the portion of soft tissue is bound to the portion of bone, the suture clamping member is pulled proximally toward inwardly extending walls defining a portion of the lumen, thereby clamping a portion of the length of suture between the inwardly extending lumen walls and the suture anchoring device.

Additional steps in the preferred method include anchoring the outer body in the blind hole, preferably by deploying ribs disposed on an outer surface of the outer body to an outwardly extended position, into surrounding cancellous bone, and cutting a portion of the suture second end to complete the procedure.

In another aspect of the invention, there is disclosed a method for securing connective tissue to bone, which comprises securing a first end of a length of suture to a portion of soft tissue to be attached to a portion of bon e, and threading a second end of the length of suture through a lumen in an outer body of a bone anchor device and about an axially movable suture clamping member disposed in a distal portion of the lumen. The bone anchor device is inserted into a blind hole disposed in the portion of bone, and a deployable anchoring member disposed on an outer surface of the outer body is extended outwardly to secure the bone anchor device in surrounding bone. Following this step, a driver portion of the bone anchor device is separated from the outer body and withdrawn from the patient's body. Then, the second end of the length of suture is pulled proximally, to secure the portion of soft tissue properly to the portion of bone and to anchor the suture in the outer body by moving the suture clamping member axially to a suture clamping position.

In still another aspect of the invention, there is provided a bone anchor device for attaching connective tissue to bone, which comprises a body having a longitudinal axis, a distal end, and a proximal end. A surface on the body distal end slopes inwardly toward the longitudinal axis from a distal portion of the surface toward a proximal portion thereof. A suture anchoring member which is movable axially toward and away from sloping surface forms a part of the bone anchor device. The suture anchoring member s a distal end surface and opposing axial surfaces, wherein the distal end and opposing axial surfaces all comprise suture receiving surfaces for contacting suture material wrapped thereabout. In essence, this means that in use, a length of suture material will be wrapped about the suture anchoring member in such a manner that the length of suture material will be in physical contact with all of the distal end surface and opposing side surfaces. In preferred embodiments, one of the opposing axial surfaces is sloped so that a width of the suture anchoring member (i.e. a dimension of the suture anchoring member which is transverse to the longitudinal axis) tapers from a distal end to a proximal end thereof.

As has been discussed supra, the sloped axial surface and the inwardly sloped body distal end surface together define a tapered distal lumen.

Now, it is to be understood that the above described invention is particularly suited to locking sutures that have been passed through soft tissues and are to be anchored to bone. The creation of an anchor point within the bone is outside the scope of this invention, although many alternative methods of anchoring suture to bone are contemplated. For example, some currently preferred methods are discussed in U.S. patent application Ser. No. 09/616,802, entitled Method & Apparatus for Attaching Connective Tissues to Bone Using a Suture Anchoring Device, filed on Jul. 14, 2000. The referenced application is commonly assigned with the present application, and is incorporated by reference in its entirety herein. Other prior art anchors, such as screws, moly bolts, and pop rivets may be adapted for use with the present invention as well.

The invention, together with additional features and advantages thereof, may best be understood by reference to the following description taken in conjunction with the accompanying illustrative drawing.

BRIEF DESCRIPTION OF THE DRAWINGS

FIG. 2. is a plan view of a second embodiment of a bone anchor having a suture lock similar to that shown in FIG. 1;

FIG. 2A is a cross-sectional view taken along lines 2A—2A of FIG. 2;

FIG. 2B is a view taken along lines 2B—2B of FIG. 2;

FIG. 3 is a plan view similar to that of FIG. 2, illustrating a first step in a preferred method for using the embodiment of FIG. 2;

FIG. 3A is a cross-sectional view taken along lines 3A—3A of FIG. 3;

FIG. 3B is a distal end view taken along lines 3B—3B of FIG. 3;

FIG. 4 is a plan view similar to that of FIG. 3, illustrating a second step in a preferred method for using the embodiment of FIG. 2;

FIG. 4A is a cross-sectional view taken along lines 4A—4A of FIG. 4;

FIG. 4B is a distal end view taken along lines 4B—4B of FIG. 4;

FIG. 6 is a plan view similar to those of FIGS. 3–5, illustrating a fourth step in a preferred method for using the embodiment of FIG. 2;

FIG. 6A is a cross-sectional view taken along lines 6A—6A of FIG. 6;

FIG. 6B is a view taken along lines 6B—6B of FIG. 6;

DESCRIPTION OF THE PREFERRED EMBODIMENT

Figure 1:
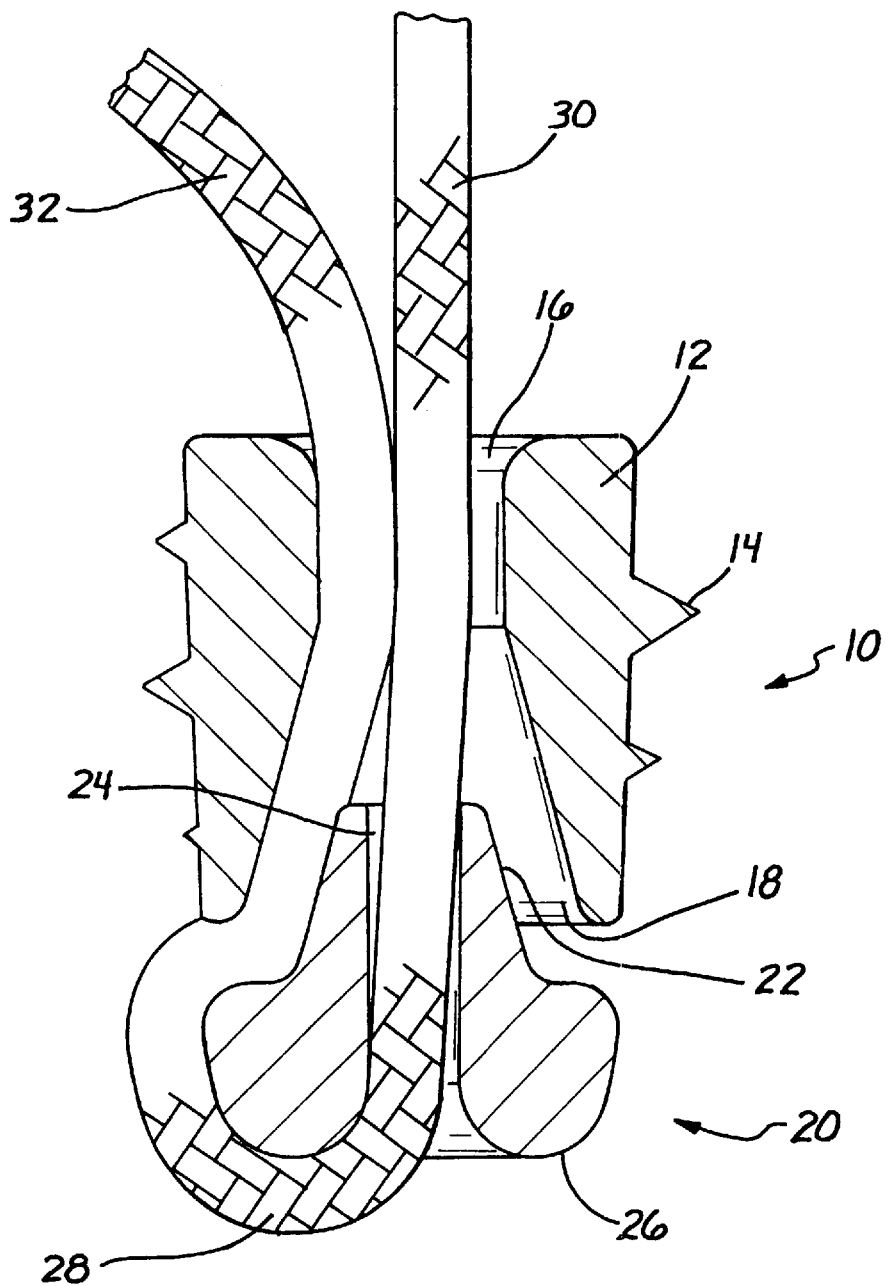
FIG. 1 is a cross-sectional view of one embodiment of a portion of a bone anchor having a suture lock constructed in accordance with the principles of the present invention.

Referring now more particularly to the drawings, there is shown in FIG. 1 a bone anchor 10 constructed in accordance with an embodiment of the present invention, comprising a body 12 which includes threads 14 on an outside surface thereof, a proximal lumen 16, and a tapered distal lumen 18 that communicates with the proximal lumen 16. A wedge body 20 includes a tapered end 22 and a lumen 24 through the wedge body 20. The lumen terminates in a large bend radius 26 at the distal end of the wedge body 20. A suture 28 which includes a bound leg 30 and a free leg 32 is threaded through the proximal lumen 16 and the wedge body lumen 24, passes around the large bend radius 26, and is redirected back through the proximal lumen 16. The bound leg 30 is considered bound because in practice, this leg of the suture is "bound" to the soft tissues to be attached to bone by virtue of passing the sutures through the tissues using conventional suturing techniques known in the art. The free leg 32 is considered "free" because the surgeon, in practice, has control over this leg of the suture with his or her hands. In turn, the pinching force on the suture 28 also increases, creating a self-locking mechanism. The threads 14 on the exterior surface of the body 12 function to secure the bone anchor in surrounding bone material.

Referring now to FIGS. 2, 2A, and 2B, a second modified embodiment of the inventive bone anchor device 110 is illustrated, wherein like elements to those shown in FIG. 1 are designated by like reference numerals, preceded by the numeral "1". The bone anchor device 110 comprises a distal wedge anchor portion 135 and a proximal driver portion 137, which are secured together mechanically in a coaxial arrangement by crimped segments 139 or other suitable means. As in the FIG. 1 embodiment, the distal wedge anchor portion 135 includes a body 112 which comprises a proximal lumen 116, a tapered distal lumen 118, and a wedge body 120 having a tapered end 122 and a large blend radius 126. A pin 141 may be disposed in a groove 142 on the wedge body 120, which is complementary to a groove 143 on an interior surface of the body 112 of the distal wedge anchor portion 135. When the pin 141 is disposed in the groove 142 and the groove 143, it functions as a retainer to keep the wedge body 120 in position in the distal lumen 118 of the device 110. This arrangement is particularly convenient when there is no suture threaded through the device, so that the device, though formed of separable elements, tends to remain unitary, thereby easing the already complicated job of the practitioner performing the repair procedure.

A crimped flat 145 on the surface of the distal portion of the body 112 creates the progressive proximal tapering in the tapered distal lumen 118, discussed supra in connection with the FIG. 1 embodiment, which is important to ensure that the suture becomes pinched between the wedge body 120 and the interior surface of the bone anchor body 112 in the tapered distal lumen 118 as the wedge body 120 moves proximally under tension, as will be described more fully hereinbelow.

Also on the outer surface of the body 112 of the bone anchor portion 135 are a plurality of slots 147, which are distributed in a spaced configuration about the entire circumference of the cylindrical body 112. These slots 147 are illustrated as being disposed at an acute angle with respect to a longitudinal axis 149 of the instrument 110, although in other preferred embodiments the slots are oriented parallel to the axis 149. Such slots and their function are more fully described in U.S. patent application Ser. No. 09/616,802, which has already been expressly incorporated herein by reference. Their function will also be described in greater detail hereinbelow.

Now with reference in particular to FIGS. 3–7, a method for using the bone anchor device 110 of FIGS. 2, 2A, and 2B to secure soft tissue to bone, for example, will be described. Initially, a suture 128, and particularly a bound leg 130 of the suture 128, is stitched in a suitable manner to a portion of soft tissue 151, such as a tendon, which is to be secured to a bone (not shown). The stitching process may be accomplished by any known means, and any known suture stitch may be employed, the objective being to ensure a secure stitch so that the suture is not inadvertently separated from the tendon after completion of the repair procedure, necessitating re-entry to the surgical site. In preferred approaches, the suture is attached to the soft tissue using a "mattress stitch", which is well known in the art as being a particularly secure stitch which is unlikely to fail postoperatively. Of course, as discussed supra, the preferred repair procedure discussed herein is an arthroscopic procedure, wherein an initial access incision is made to the repair site, such as a shoulder, and a trocar is inserted into the access incision to provide access to the repair site for surgical instruments as well as optical instruments. Preferably, a suturing instrument is inserted into the trocar to perform the aforementioned suturing step. Of course, the inventive devices may also be utilized in an open surgical procedure, if desired, wherein the sutures are manually placed.

Once the suturing process is completed, a free end 132 of the suture 128 is removed proximally through the trocar from the patient's body, together with the suturing instrument. The free end 132 of the suture is then threaded through a lateral port 153 and then through the proximal lumen 116 of the bone anchor instrument 110 (FIGS. 3, 3A, and 3B). It is threaded distally through the tapered distal lumen 118 and around the distal end surface (large blend radius) 126 of the wedge body 120, then proximally back through the tapered distal lumen 118 and through the lumen 116 to the proximal end of the driver portion 137. It is noted that, in this embodiment, the wedge body 120 does not include a wedge lumen, as in the FIG. 1 embodiment. Rather, the suture is threaded about the wedge body, so that it is in physical contact with the large blend radius 126, as well as with each opposing side surface 154a, b (FIG. 4A) of the wedge body. However, the wedge body could be modified to include a wedge lumen, and the suture could be threaded therethrough, as in the FIG. 1 embodiment, if desired.

Once the threading process is completed, the bone anchor instrument 110 is returned through the trocar (not shown) to the repair site, and the distal wedge anchor portion 135 is placed into a blind hole (not shown) which has been made, preferably by drilling, into the bone to which the soft tissue 151 is to be secured.

With reference now to FIGS. 4, 4A, and 4B, once the distal wedge anchor portion 135 is satisfactorily disposed within the bone (not shown), the driver portion is actuated to radially outwardly deploy a plurality of ribs 157 which comprise the portions of the body 112 which lie between the aforementioned spaced slots 147. This procedure is more fully described in co-pending U.S. patent application Ser. No. 09/616,802, already incorporated herein by reference, but, essentially, the deployment is made by axially compressing the distal wedge anchor portion to thereby force the ribs 157 radially outward. In a preferred embodiment, wherein, as mentioned supra, the slots 147 lie at an angle with the longitudinal axis 149 of the device 110, the resulting "petals" formed by the radially outwardly extending ribs 157 take on a semi-circular shape, with the "petals" overlapping one another to create an extraordinarily strong anchor body. The soft cancellous bone into which the anchor body is radially extended tends to flow between the "petals" as well, further strengthening the achieved anchoring effect both axially and radially. The anchor should be radially deployed beneath the cortical bone surface, so that it is virtually impossible to retract the distal wedge anchor portion from the bone proximally past the cortical outer surface thereof without breaking the native bone.

Figure 5:
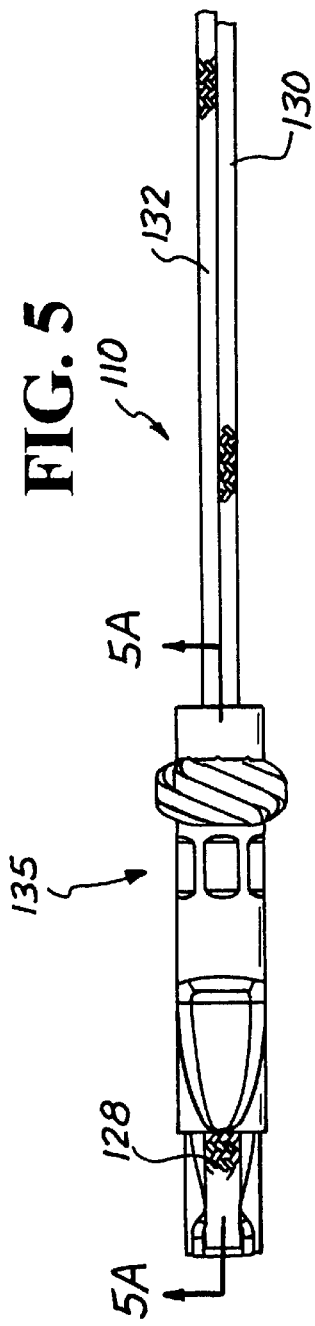
FIG. 5 is a plan view similar to those of FIGS. 3 and 4, illustrating a third step in a preferred method for using the embodiment of FIG. 2.
Figure 5A:
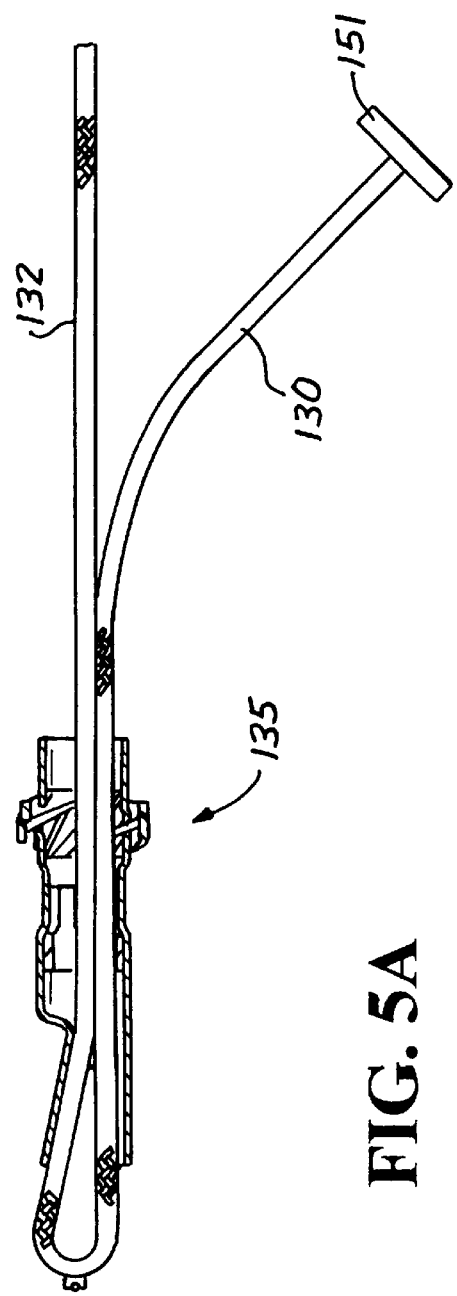
FIG. 5A is a cross-sectional view taken along lines 5A—55A of FIG. 5.

A unique and important feature of the present invention is the provision of a stress point 159 in the junction between the distal wedge anchor portion 135 and the proximal driver portion 137. The reason for this is that, once the driver portion has been utilized to position the wedge anchor portion, and then actuated to axially compress the wedge anchor portion, so that the anchor ribs 157 are radially extended, there is no more purpose for the driver portion. As mentioned supra, the wedge anchor portion 135 and driver portion 137 are mechanically joined by, for example, a plurality of crimped segments 139, which create an interfering fit between the axially overlapping cylindrical bodies of each of the two portions 135, 137. Of course, many other equivalent joinder means may be employed as well, and these means will be well known to those of ordinary skill in the art. In the presently preferred embodiment, however, the stress point 159 is co-located with the crimped segments 139, and designed so that, as the compressing force is applied by the driver portion 137 to the wedge anchor portion 135, to radially deform and extend the ribs 157, when it reaches a level somewhat above the force level required to complete the anchor deployment, the stress point which is a pr-edesigned point of weakness or "failure point", will break, physically separating the driver portion 137 from the anchor portion 135. FIGS. 5 and 5A illustrate the device 110 after the driver portion 137 has been separated from the wedge anchor portion 135 and withdrawn proximally from the patient's body through the trocar (not shown).

Thus, the wedge anchor portion 135 is now permanently deployed in the bone, to thereby securely anchor the suture 128 therein, and thus permanently secure the soft tissue 151 to the bone.

With reference now to FIGS. 6, 6A, and 6B, it will be seen that, once the distal anchor portion 135 is secured within the bone, it is time for the practitioner to pull the free ends 132 of the suture 128 proximally, to draw the soft tissue 151 toward the bone until it is snugly situated in desired proximity thereto, thereby creating a tight and secure connection between the soft tissue and the bone. As discussed supra, with respect to the FIG. 1 embodiment, the bound leg 130 of the suture follows through the bone anchor, about the wedge body 120, until such time as the tissues 151 binding in the bound leg 130 of the suture 128 create a tension in the suture 128. This will occur when the soft tissue 151 has been drawn toward the bone and is snugly situated with respect thereto. At this point, tension in the suture 128 tends to urge the wedge body 120 proximally, up into the tapered distal lumen 118, as shown in FIG. 6A, pinching the suture 128 between an inwardly sloping surface 161 (FIG. 4A) on the body 112 and the sloping axial surface 154a on the tapered end 122 of the wedge body 120, within the tapered distal lumen 118. As the tension in the bound leg 130 of the suture 128 increases, the proximal force on the wedge body 120 increases. In turn, the pinching force on the suture 128 also increases, creating a self-locking mechanism.

It may be helpful to discuss in some detail this self-locking suture mechanism. One of the significant advantages of this mechanism is its reversibility; i.e. its ability to permanently lock the bound end of the suture in position, but to permit continued adjustability of the suture loop by applying a tensile force to the free end of the suture; This is important, because a practitioner will often find that, during the course of a procedure, after the tendon/soft tissue 151 has been brought into what is believed to be a desired position relative to the bone to which it is being secured, and the suture has been locked into place to retain the tendon in that orientation, a further adjustment is necessary or desired to optimize the outcome. Using existing prior art solutions, though, wherein the suture is knotted into position and fixed at a particular length, it would be necessary to either forego the desired adjustment or, alternatively, to cut the suture and re-suture the tendon. In some instances, it may be necessary to abandon the suture anchor, leaving the useless (and expensive) anchor in position, and locating a new anchor in the bone to re-suture the tendon.

On the other hand, in the present invention, after the free end 132 has been pulled, as described above, sufficiently that a tension is created in the bound end 130 (due to approximation of the tendon 151 to the bone), and the suture 128 has been clamped in the tapered distal lumen 118, only the bound end 130 is anchored in a fixed position. This ensures that the tendon is not movable relative to the bone after completion of the procedure, which, of course, is desirable. On the other hand, the free end 132 continues to be movable, to thereby permit adjustment of the size of the suture loop through the tendon 151, which in turn permits adjustment or "fine tuning" of the position of the tendon 151 with respect to the bone.

Figure 6D:
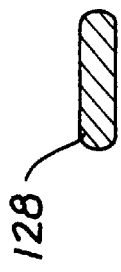
FIG. 6D is a cross-sectional view illustrating the suture of FIG. 6C after it has been clamped and compressed by the wedge clamp of the present invention.
Figure 6C:
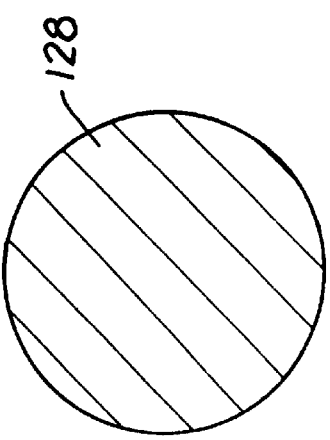
FIG. 6C is a cross-sectional view of one type of suture material which may be used in the present invention.

To understand this advantageous feature, it may be helpful to review in a bit more detail the functionality of the inventive device and method. Again with reference to FIGS. 2–6B, it may be seen that, in the early procedural steps, both the free and bound suture legs are freely movable to slide the suture 128 about the free-floating anchor wedge 120. However, once tension develops in the bound leg 130 as the tendon 151 approximates the bone, the wedge 120 is pulled proximally to clamp a length of the suture 128 within the tapered distal lumen 118, as discussed in detail supra. Applying a tensile force to the bound leg at this juncture only enhances the clamping effect by proximally pulling the wedge 120 even more tightly against the clamped length of suture 128. FIGS. 6C and 6D illustrate the effect of this clamping force on the clamped length of suture 128, as observed by the inventor. In the case where #2 round suture is utilized, having a cross-sectional width of 0.023 inches, as shown in FIG. 6C, the clamping force exerted by the wedge block 120 against the clamped length of suture causes it to flatten and compress to a width of approximately 0.011 inches.

On the other hand, now the free leg 132 of the suture 128 may continue to be manipulated to adjust the size of the suture loop at the bound end. Applying a tensile force to the free leg 132, once the suture is clamped by the wedge 120, causes the wedge 120 now to move again in a distal direction, thereby increasing the cross-sectional area of the tapered lumen 118, so that the clamped length of suture may slide to adjust the positioning of the bound suture end. There are two apparent reasons for this response. One is that, when the free end 132 is pulled, the clamped length of suture 128 wants to straighten out, so that it pushes against the angled inner lumen wall which forms, in part, the tapered distal lumen 118. Since this wall is fixed in position, a reactive force pushes against the tapered face of the wedge 120, pushing it a modest distance distally. Another reason is that continued tension on the free end of the suture results in a return of the cross-sectional area of the clamped suture portion from a reduced flat cross-section to the original larger round cross-section. This rounding effect reduces the surface contact of the suture with the adjacent lumen walls (and resultant frictional interface), making it easier for the suture to slide through the tapered lumen. Also, the increased suture diameter pushes the wedge 120 a slight distance distally. The resultant larger tapered lumen permits free sliding of the suture 128 until a desired adjustment has been made, after which the tendon 151 is again clamped as explained supra.

Figure 7:
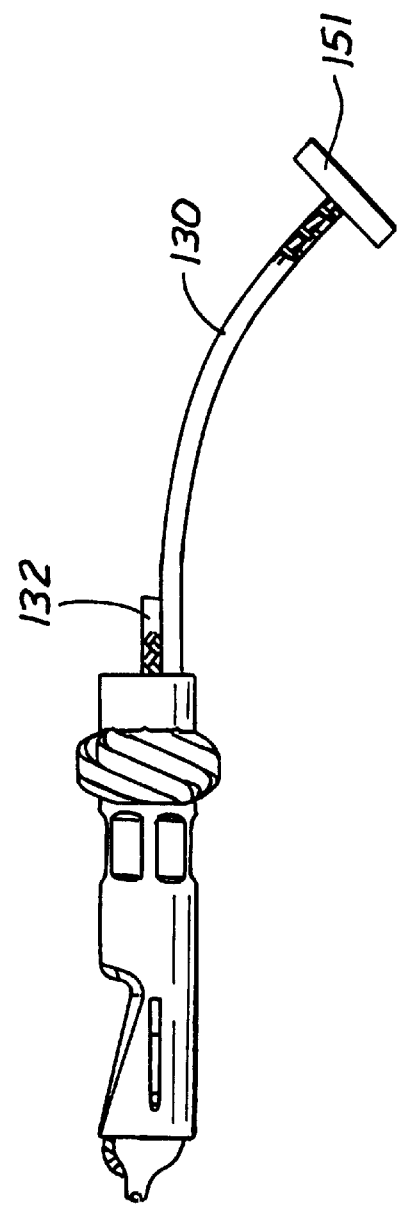
FIG. 7 is a plan view similar to those of FIGS. 3–6, illustrating a fifth step in a preferred method for using the embodiment of FIG. 2.

Now referring to FIG. 7, the final step in the sequence of permanently anchoring the soft tissue 151 to bone is illustrated, wherein, once the suture is locked in place by virtue of the proximal positioning of the wedge body 120 within the anchor portion 135, the free end 132 is cut off near the proximal end of the anchor portion 135, and the incision is closed. The free end 132 is only cut off after all final adjustments have been made, as discussed above, so that the tendon is precisely positioned as desired.

FIGS. 8–15 illustrate a procedure similar to that shown in FIGS. 2–7, but specifically adapted for repair of a patient's rotator cuff, arthroscopically. Accordingly, like elements to those illustrated in previous figures will be designated by the same reference numerals, preceded by the numeral "2".

Figure 8:
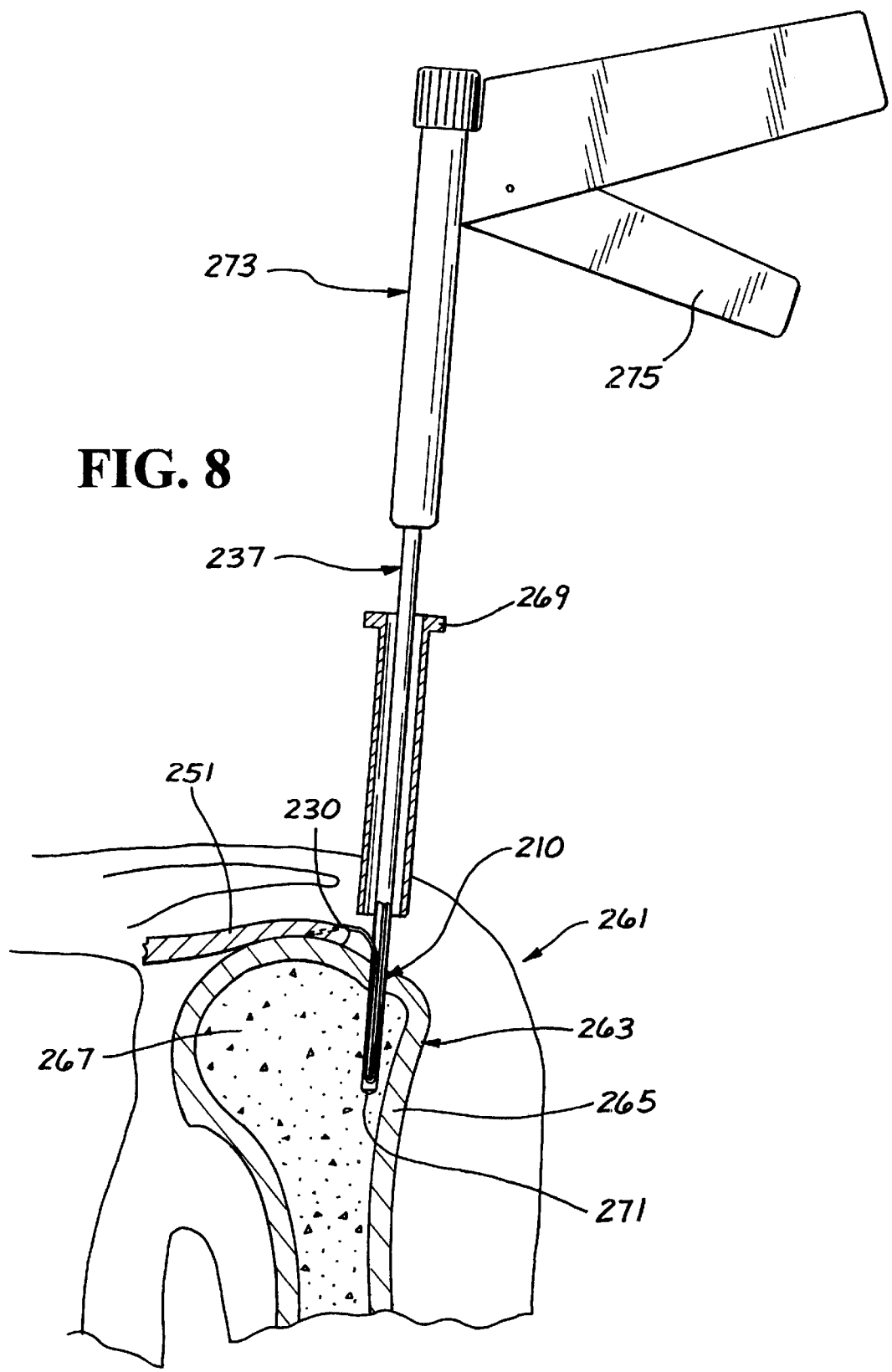
FIG. 8 is a schematic view illustrating a first step in a preferred method for using a suture lock and bone anchor constructed in accordance with the present invention to repair a torn rotator cuff arthroscopically.

Thus, there is shown in FIG. 8 a shoulder 261, which comprises a humeral head 263, including an outer cortical bone layer 265, which is hard, and inner cancellous bone 267, which is relatively soft. As is typically the case for rotator cuff injuries, in this instance the supraspinatus tendon 251 has become separated from the humeral head 263, and the objective of the rotator cuff repair procedure is to reattach the tendon 251 to the humeral head 263.

Alternate rotator cuff repair procedures are also discussed in U.S. patent application Ser. No. 09/475,495, filed on Dec. 30, 1999, and entitled Method and Apparatus for Attaching Connective Tissues to Bone Using a Knotless Suture Anchoring Device, which is herein expressly incorporated by reference.

To effect the rotator cuff repair, the practitioner will first create an incision in the patient's shoulder 261, into which will be inserted a trocar 269, as shown in FIG. 8. The trocar permits access to the procedural site for visualization instruments, as well as working instruments, and permits the procedure to be completed arthroscopically.

Figure 9:
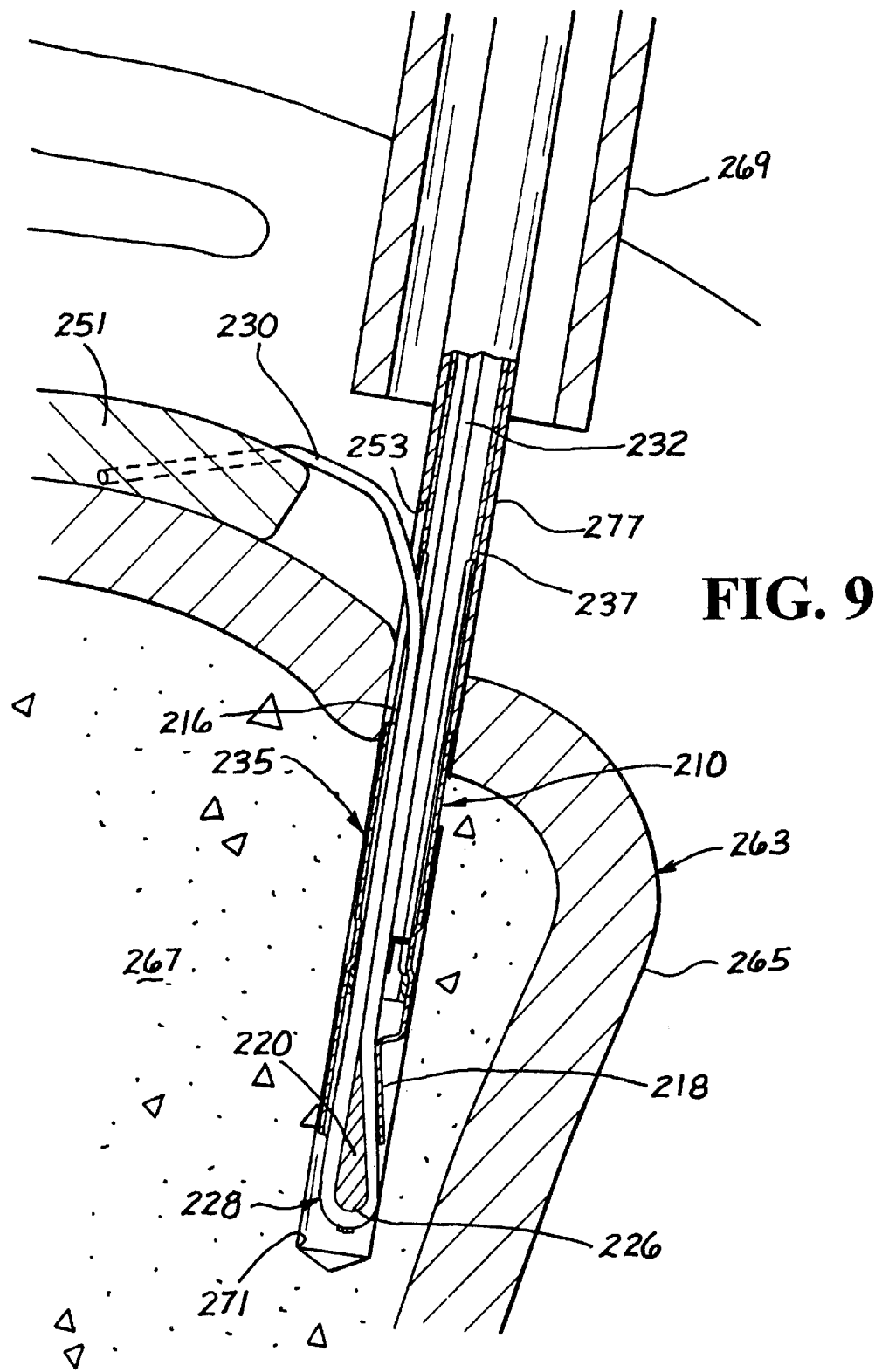
FIG. 9 is an enlarged schematic view illustrating the distal end of the instrument shown in FIG. 8.

Again, as in the embodiment shown in FIGS. 3–7, once the trocar has been inserted, the first procedural step is to suture the tendon 251, using desired techniques which are beyond the scope of this patent application, creating a bound suture end 230 (FIGS. 8 and 9). Once this suturing step is completed, as with the FIGS. 3–7 embodiment, the free end 232 (FIG. 9) of the suture 228 is removed proximally through the trocar from the patient's body, together with the suturing instrument (not shown). The free end 232 of the suture is then threaded through the proximal lumen 216 of the bone anchor instrument 210 through a lateral port 253, distally through the tapered distal lumen 218 and around the large blend radius 226 of the wedge body 220, then proximally back through the tapered distal lumen 218 and through the lumen 216 to the proximal end of a driver portion 237. Once the threading process is completed, the bone anchor instrument 210 is returned through the trocar 269 to the repair site, and the distal wedge anchor portion 235 is placed into a blind hole 271 which has been made, preferably by drilling, into the bone 263 to which the soft tissue tendon 251 is to be secured.

Figure 10:
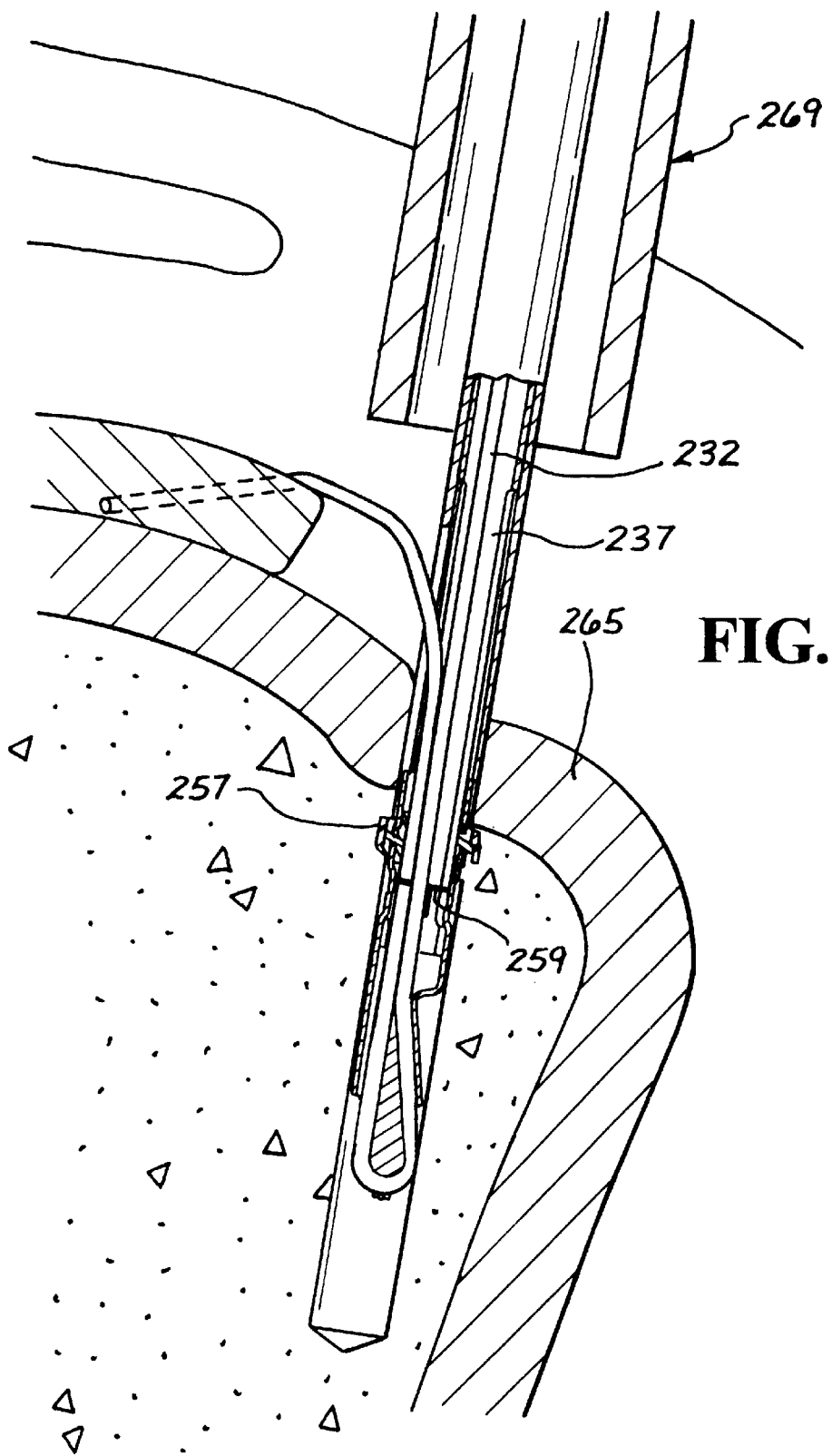
FIGS. 10–14 are views similar to FIG. 9 illustrating sequential steps in the aforementioned method.

With reference now to FIG. 10, once the distal wedge anchor portion 235 is satisfactorily disposed within the bone 263, beneath the cortical layer 265, the driver portion 237 is actuated to radially outwardly deploy a plurality of ribs 257 to create a "flower" comprised of a plurality of "petals", which have a diameter substantially larger than the diameter of the hole 271, thereby preventing "bac-kout" of the anchor portion 235 from the hole 271. Although many different actuation mechanisms may be employed, the illustrated embodiment shows a handle portion 273 (FIG. 8) including a trigger 275, which may be squeezed by the practitioner to axially compress the anchor portion 235 and thereby deploy the "flower" anchor. This procedure is the same as that employed in the FIGS. 3–7 embodiment.

Figure 11:
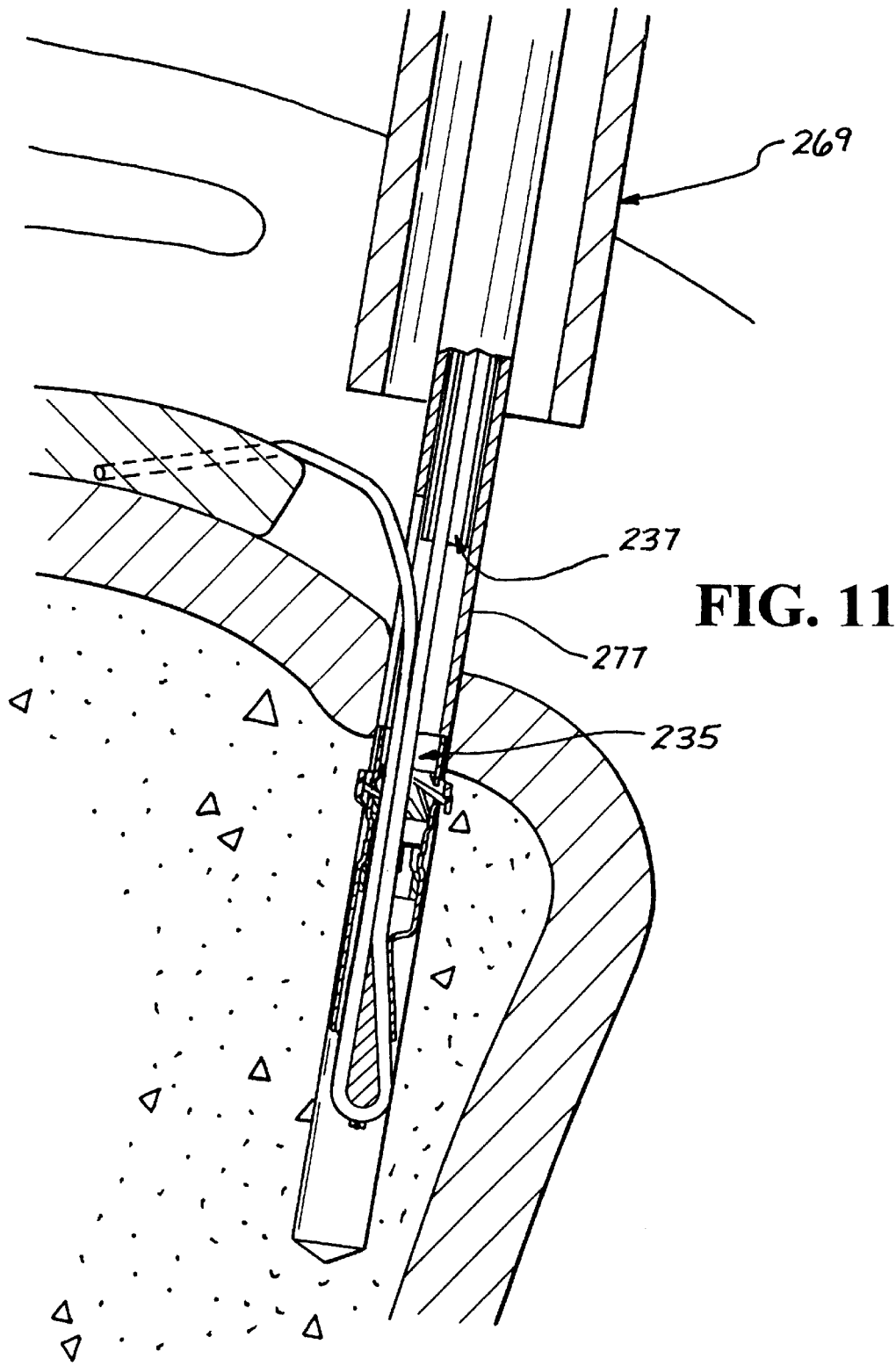

As in the FIGS. 3–7 embodiment, a stress point 259 is provided in the junction between the distal wedge anchor portion 235 and the proximal driver portion 237. Referring now to FIG. 11, then, as in the prior embodiment, once the wedge anchor portion has been fully compressed to fully radially extend the anchor ribs 257, the trigger 275 continues to be squeezed for a period of time to exert continuing axial compression force on the column of the wedge anchor portion 235. This continued force application will cause the column to fail at its designed failure point, namely, the stress point 259, so that the driver portion 237 becomes physically separated from the anchor portion 235. As shown in FIG. 11, once the driver portion 237 is physically separated from the anchor portion 235, it is withdrawn proximally through the trocar 269, out of the patient's body. In FIG. 11, the driver portion 237 is shown partially withdrawn, and in FIG. 12 it is fully withdrawn. It is noted that, in this embodiment, a suture channel 277 is disposed coaxially about the driver portion 237, as shown.

Thus, the wedge anchor portion 235 is now permanently deployed in the bone 263, to thereby securely anchor the suture 228 therein, and thus permanently secure the soft tissue 251 to the bone 263.

Figure 12:
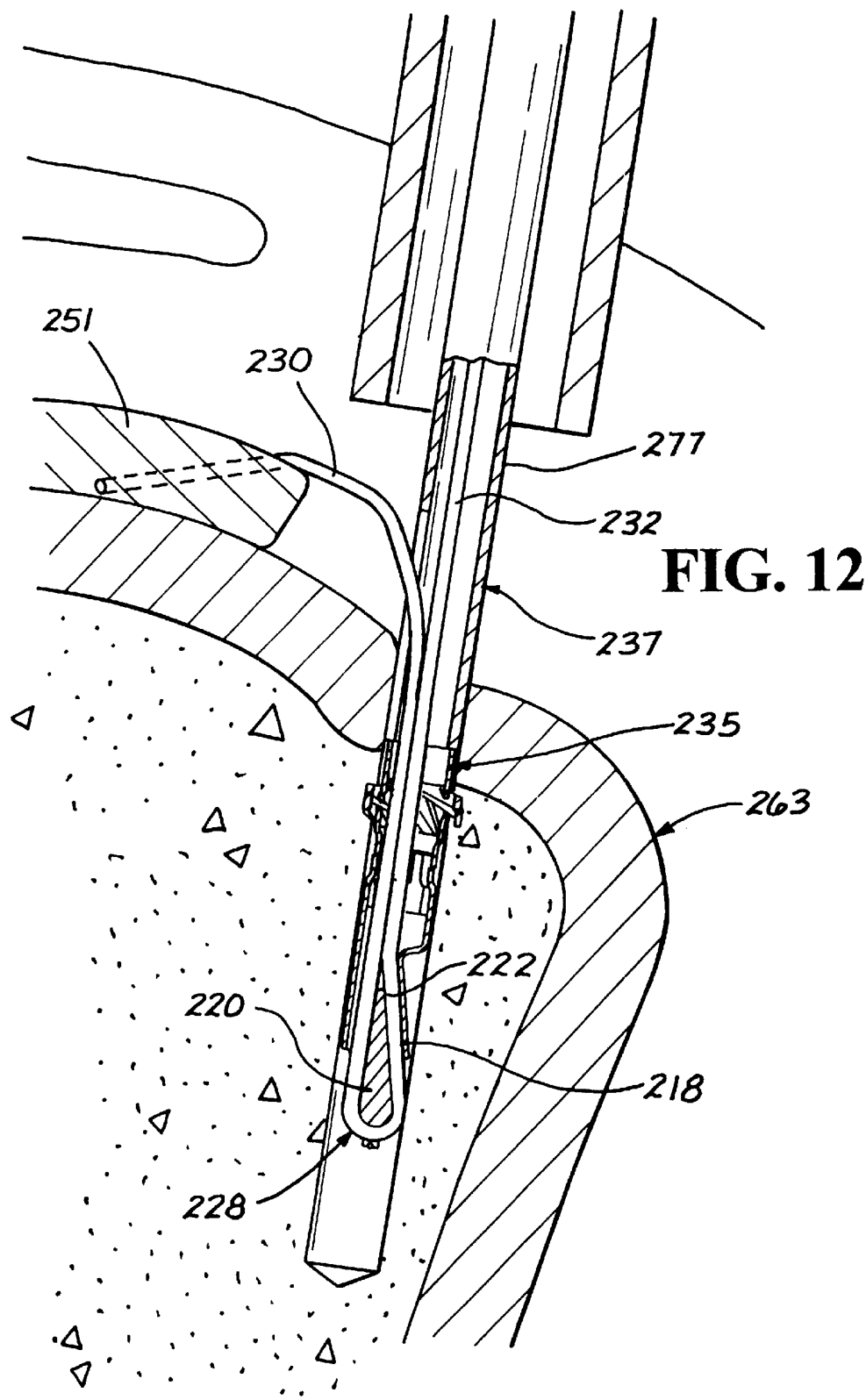
Figure 13:
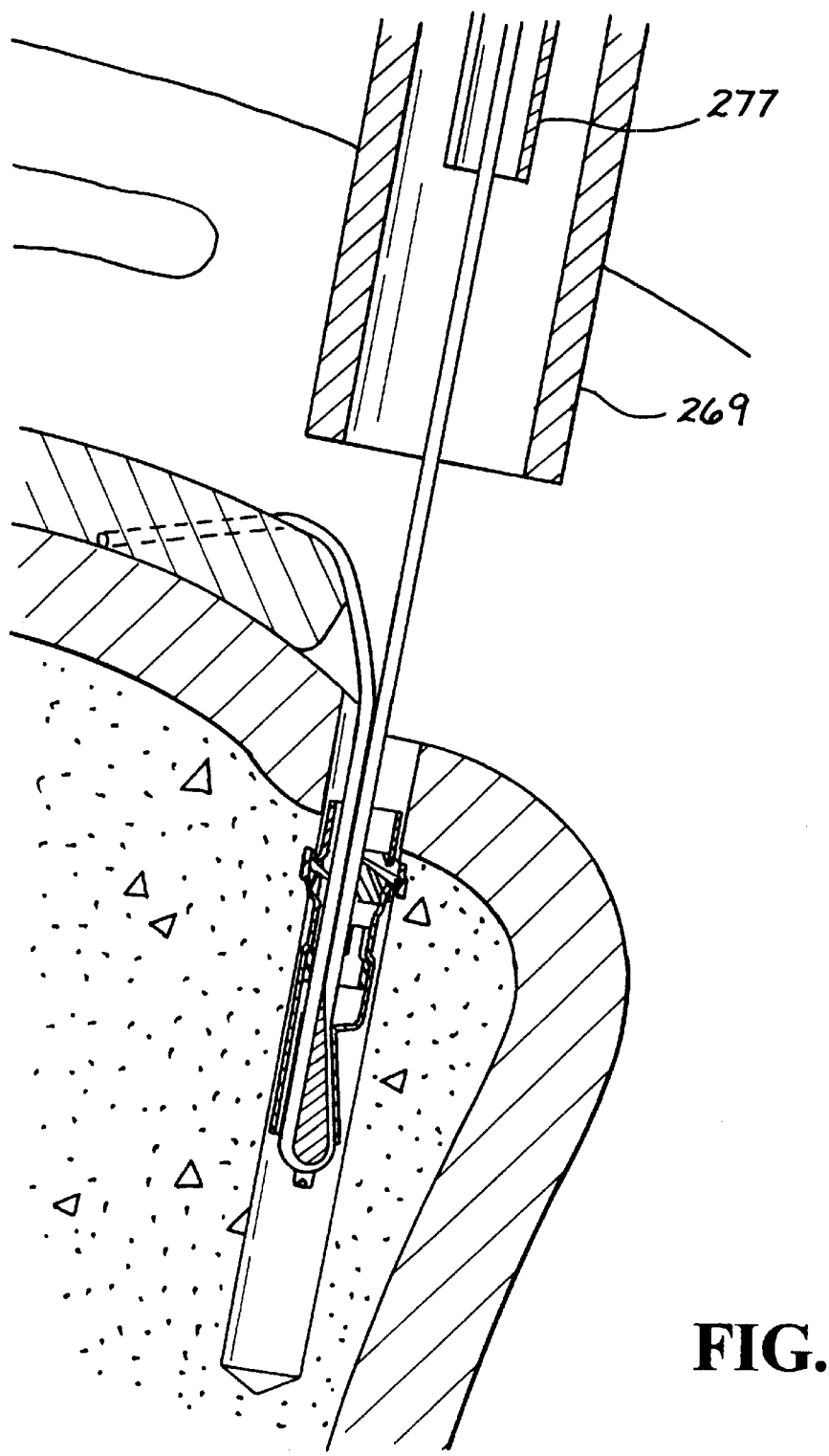

With reference now to FIGS. 12 and 13, it will be seen that, once the distal anchor portion 235 is secured within the bone 263, it is time for the practitioner to pull the free end 232 of the suture 228 proximally, to draw the tendon 251 toward the bone 263 until it is snugly situated in desired proximity thereto, thereby creating a tight and secure connection between the tendon and the bone. As discussed supra, with respect to prior embodiments, the bound leg 230 of the suture follows through the bone anchor, about the wedge body 220, until such time as the tendon 251 binding in the bound leg 230 of the suture 228 creates a tension in the suture 228. At this point, tension in the suture 228 tends to urge the wedge body 220 proximally, up into the tapered distal lumen 218, as shown in FIG. 12, pinching the suture 228 between the tapered distal lumen 218 and the tapered end 222 of the wedge body 220. As the tension in the bound leg 230 of the suture 228 increases, the proximal force on the wedge body 220 increases. In turn, the pinching force on the suture 228 also increases, creating a self-locking mechanism.

Figure 14:
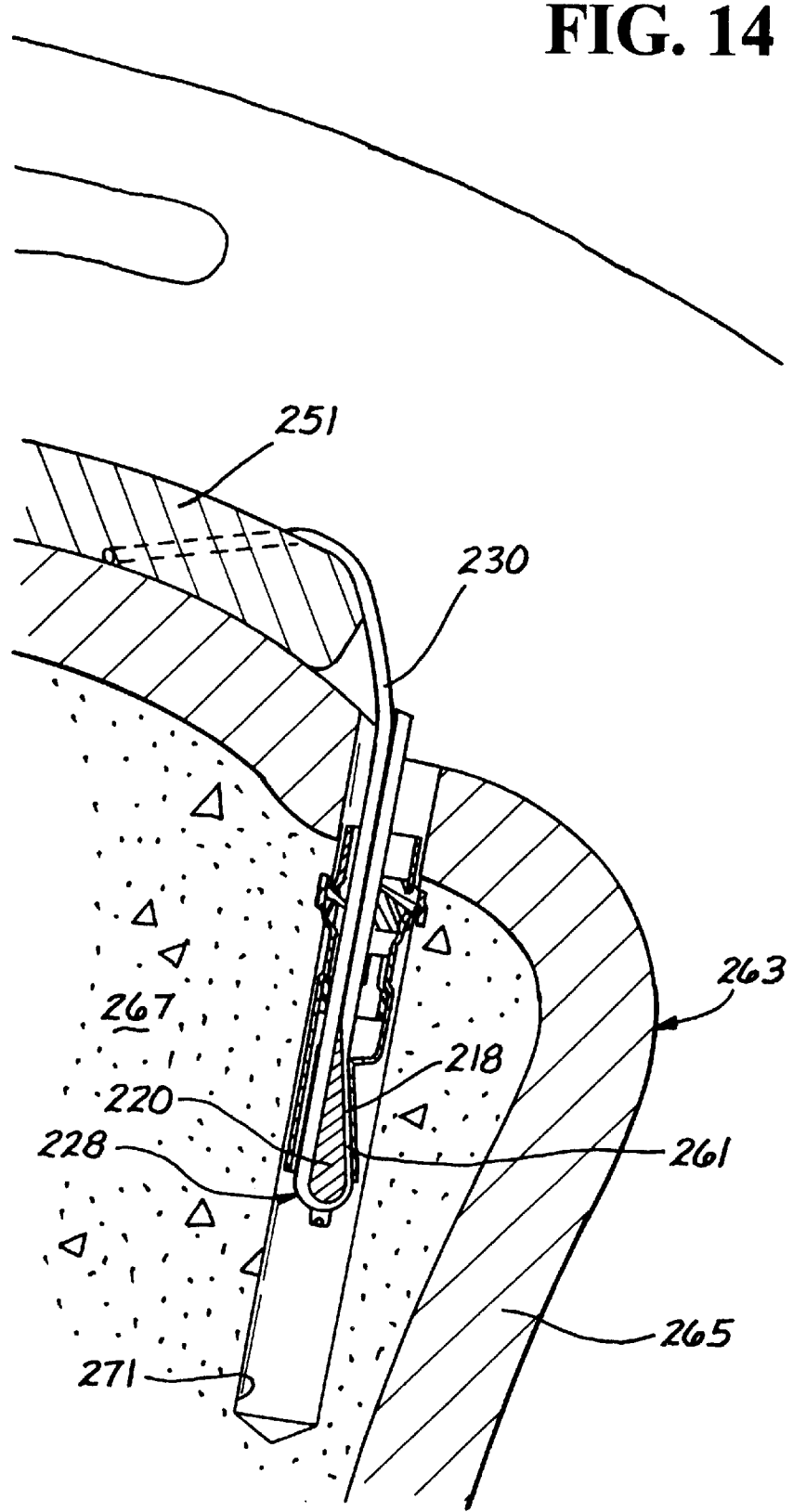
Figure 15:
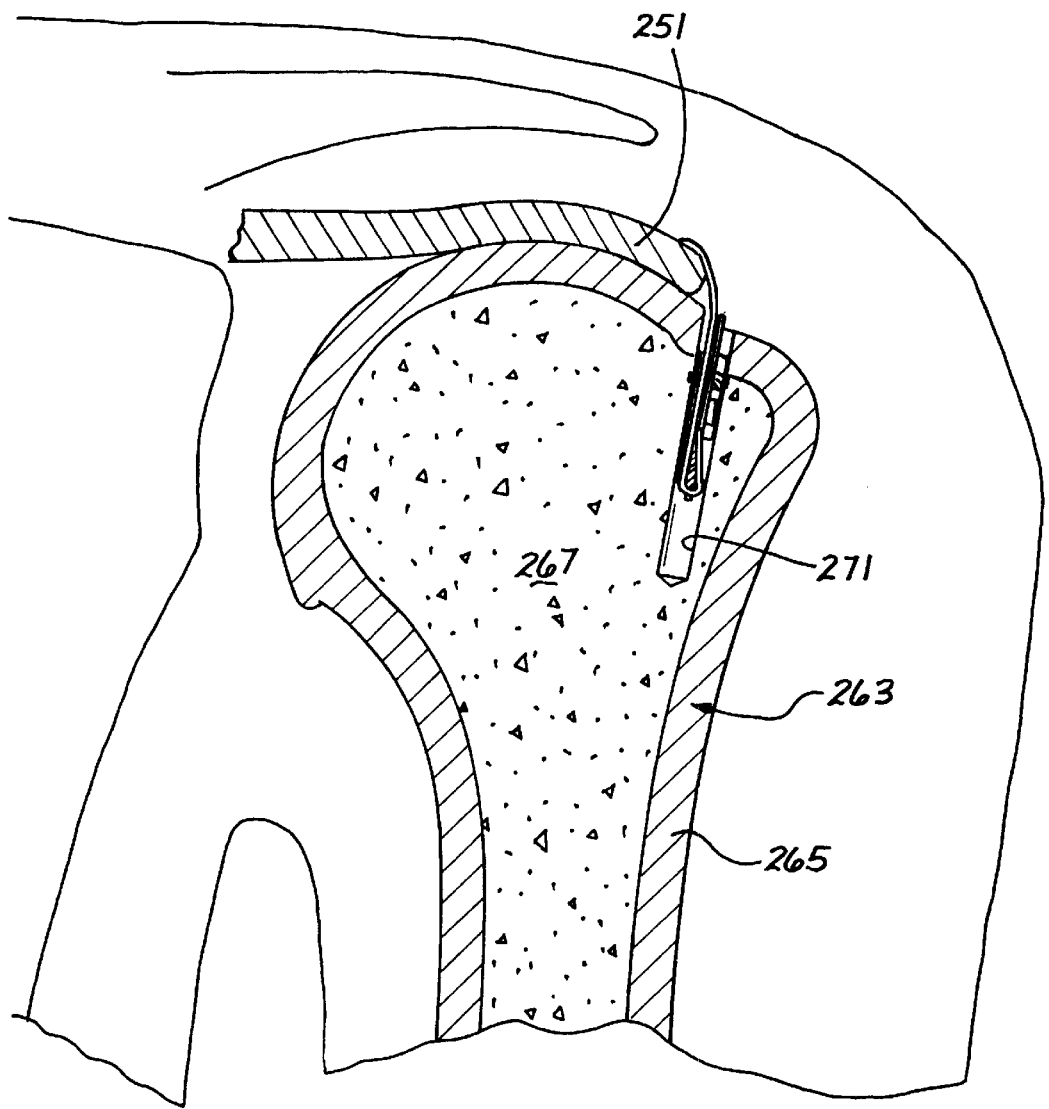
FIG. 15 is a schematic view similar to FIG. 8 illustrating the repaired rotator cuff at the conclusion of the aforementioned method.

Now referring to FIG. 13, once the suture 228 is locked in place within the bone anchor portion 235, the suture channel 277 is proximally withdrawn through the trocar 269. Then, as shown in FIGS. 14 and 15, the excess suture material on the free leg 232 is cut off, the trocar is removed, and the incision is closed to complete the procedure.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A bone anchor device for attaching connective tissue to bone, comprising:

an outer body having an outer surface and having a protrusion thereon extending outwardly to anchor said outer body in a bone;

a lumen extending axially through said outer body, said lumen being defined by inner walls and having a smaller cross-section in a proximal portion of said outer body than in a distal portion thereof, such that at least portions of said inner walls taper inwardly in a proximal direction; and an elongated wedge member disposed in a distal end of said lumen, said wedge member having outer walls which taper inwardly in a proximal direction there along, such that a proximal portion of said wedge member has a smaller cross-section than a distal portion of said wedge member, said wedge member being axially movable in said lumen distal end.

2. The bone anchor device as recited in claim 1, wherein said protrusion comprises a thread.

3. The bone anchor device as recited in claim 1, wherein said protrusion comprises a plurality of outwardly extendable ribs.

4. The bone anchor device as recited in claim 1, and further comprising a lumen extending axially through said wedge member, in substantially the same directional orientation as said outer body lumen, for receiving a suture therein.

5. The bone anchor device as recited in claim 1, wherein said wedge member comprises a distal end having a curved surface.

6. The bone anchor device as recited in claim 1, wherein the tapered proximal surface of said wedge member and said inwardly tapered lumen internal wall together define a tapered distal lumen which communicates with said outer body lumen.

7. The bone anchor device as recited in claim 6, and further comprising a suture extending through said outer body lumen and around a distal surface of said wedge member, said suture including a free end extending proximally out of said bone anchor device and a bound end attached to soft tissue to be secured to said bone, wherein when said free end is placed in tension by a proximally directed force, the suture travels about said wedge member until increased tension on said bound end causes said suture to move said wedge member axially in a proximal direction, the proximal axial travel of said wedge member continuing until the proximal surface of the wedge member has moved into sufficient proximity to the inwardly tapered internal lumen wall to pinch a length of said suture in said tapered distal lumen.

8. A bone anchor device for attaching connective tissue to bone, comprising:

an outer body;

a lumen extending axially through said outer body, wherein inner walls which define said lumen in a proximal portion of said outer body extend inwardly relative to inner walls which define said lumen in a portion of said outer body distal to said proximal portion;

a suture clamping member comprising a wedge member which is axially movable in said lumen distal portion; and a suture extending through said lumen and around a distal surface of said wedge member, said suture including a free end extending proximally out of said bone anchor device and a bound end attached to soft tissue to be secured to said bone, wherein when said free end is placed in tension by a proximally directed force, the suture travels about said wedge member until increased tension on said bound end causes said suture to move said wedge member axially in a proximal direction, the proximal axial travel of said wedge member continuing until the proximal surface of the wedge member has moved into sufficient proximity to the inwardly extending internal lumen wall to pinch a length of said suture therebetween.

9. The bone anchor device as recited in claim 8 wherein said wedge member distal surface is curved.

10. The bone anchor device as recited in claim 8, wherein said outer body has an outer surface, said outer surface having outwardly extendable ribs disposed thereon for anchoring said outer body in bone.

11. The bone anchor device as recited in claim 8, and further comprising a lumen extending axially through said wedge member for receiving a suture therein.

12. A bone anchor device for attaching connective tissue to bone, comprising:
   an outer body having an open distal end;
   a lumen extending axially through said outer body, wherein inner walls which define said lumen in a proximal portion of said outer body extend inwardly relative to inner walls which define said lumen in a portion of said outer body distal to said proximal portion;
   a suture clamping member having an outer surface, said suture clamping member being disposed in said lumen distal end and being axially movable therein; and
   complementary engaging structure disposed on each of said suture clamping member outer surface and said lumen inner surface for retaining said suture clamping member in said lumen distal end when the bone anchor device is not in a portion of bone, said complementary engaging structure comprising a pin disposed on one of said suture clamping member outer surface and said lumen inner surface, and a recess for receiving the pin disposed on the other of said suture clamping member outer surface and said lumen inner surface.

13. A bone anchor device for attaching connective tissue to bone, comprising:
   an outer body having an outer surface;
   a lumen extending axially through said outer body, wherein inner walls which define said lumen in a proximal portion of said outer body extend inwardly relative to inner walls which define said lumen in a portion of said outer body distal to said proximal portion;
   a suture clamping member disposed in said lumen distal portion and being axially movable therein; and
   at least one outwardly extendable rib disposed on said outer body outer surface for anchoring said outer body into surrounding bone, wherein said inner walls which define said outer body lumen do not move outwardly when said at least one outwardly extendable rib is extended outwardly.

14. The bone anchor device as recited in claim 13, wherein said at least one outwardly extendable rib comprises a plurality of outwardly extendable ribs.

15. The bone anchor device as recited in claim 13, said suture clamping member comprising a wedge member having outer walls which taper inwardly in a proximal direction therealong.

16. The bone anchor device as recited in claim 13, and further comprising a suture extending through said lumen and around a distal surface of said suture clamping member, said suture including a free end extending proximally out of said bone anchor device and a bound end attached to soft tissue to be secured to said bone, wherein when said free end is placed in tension by a proximally directed force, the suture travels about said suture clamping member until increased tension on said bound end causes said suture to move said suture clamping member axially in a proximal direction, the proximal axial travel of said suture clamping member continuing until a proximal surface of the suture clamping member has moved into sufficient proximity to the inwardly extending internal lumen wall to pinch a length of said suture in a tapered distal lumen disposed between said suture clamping member proximal surface and the inwardly extending internal lumen wall.

17. The bone anchor device as recited in claim 13, wherein said outer body comprises a distal anchor portion and said device further comprises a proximal driver portion connected to a proximal end of said distal anchor portion.

18. The bone anchor device as recited in claim 17, wherein said proximal driver portion comprises an actuator for outwardly extending said at least one outwardly extendable rib.

19. The bone anchor device as recited in claim 18, wherein the connecting joint between said distal anchor portion and said proximal driver portion includes a designed failure point, so that upon deployment of said at least one outwardly extendable rib to its extended position, additional force may be applied to separate the driver portion from the anchor portion so that only the driver portion may be proximally removed from the patient's body.

20. A bone anchor device for attaching connective tissue to bone, comprising:
   a distal wedge anchor portion comprising an outer body having an outer surface, on which an outwardly deployable anchoring element is situated;
   a proximal driver portion connected to said distal wedge anchor portion at a proximal end thereof, said driver portion including an actuator for deploying said anchoring element outwardly, wherein the connection between said proximal driver portion and said distal wedge anchor portion is releasable once the anchoring element has been deployed;
   a suture clamping member movable within said distal wedge anchor portion; and
   a length of suture disposed in proximity to said suture clamping member.

21. The bone anchor device as recited in claim 20, and further comprising a designed failure point in the connection between the proximal driver portion and the distal wedge anchor portion, so that upon deployment of said anchoring element outwardly, additional force may be applied to separate the driver portion from the anchor portion so that only the driver portion may be proximally removed from the patient's body.

22. The bone anchor device as recited in claim 20, said distal wedge anchor portion further comprising a lumen extending axially through said outer body, wherein inner walls which define said lumen in a proximal portion of said outer body taper inwardly relative to inner walls which define said lumen in a portion of said outer body distal to said proximal portion; and
   said suture clamping member is disposed in said lumen distal portion and is axially movable therein.

23. The bone anchor device as recited in claim 22, wherein said length of suture extends through said lumen and around a distal surface of said suture clamping member, said suture including a free end extending proximally out of said bone anchor device and a bound end attached to soft tissue to be secured to said bone, wherein when said free end is placed in tension by a proximally directed force, the suture travels about said suture clamping member until increased tension on said bound end causes said suture to move said suture clamping member axially in a proximal direction, the proximal axial travel of said suture clamping member continuing until a proximal surface of the suture clamping member has moved into sufficient proximity to the inwardly extending internal lumen wall to pinch a length of said suture in a tapered distal lumen disposed between said suture clamping member proximal surface and the inwardly extending internal lumen wall.

24. A method for securing connective tissue to bone, comprising:

securing a first end of a length of suture to a portion of soft tissue to be attached to a portion of bone;

threading a second end of the length of suture through a lumen in an outer body of a bone anchor device and about an axially movable suture clamping member disposed in a distal portion of said lumen;

placing said outer body in a blind hole disposed in said portion of bone; and pulling the second end of the length of suture proximally, so that the suture travels about the axially movable suture clamping member and draws the first end of the length of suture toward the bone anchor device, thereby securing the portion of soft tissue snugly to the portion of bone;

wherein when the tension on the first end of the length of suture increases, as the portion of soft tissue is bound to the portion of bone, the suture clamping member is pulled proximally toward inwardly extending walls defining a portion of said lumen, thereby clamping a portion of the length of suture between the inwardly extending lumen walls and the suture anchoring device.

25. The method as recited in claim 24, and further comprising a step of anchoring said outer body in said blind hole.

26. The method as recited in claim 25, wherein said anchoring step is accomplished by deploying ribs disposed on an outer surface of said outer body to an outwardly extended position.

27. The method as recited in claim 24, and further comprising a step of cutting a portion of the suture second end to complete the procedure.

28. A method for securing connective tissue to bone, comprising:

securing a first end of a length of suture to a portion of soft tissue to be attached to a portion of bone;

threading a second end of the length of suture through a lumen in an outer body of a bone anchor device and about an axially movable suture clamping member disposed in a distal portion of said lumen;

inserting said bone anchor device into a blind hole disposed in said portion of bone;

extending a deployable anchoring member disposed on an outer surface of said outer body outwardly to secure said bone anchor device in surrounding bone;

separating a driver portion of said bone anchor device from said outer body and withdrawing said driver portion from the patient's body; and pulling the second end of the length of suture proximally, to secure the portion of soft tissue properly to the portion of bone and to anchor the suture in said outer body by moving the suture clamping member axially to a suture clamping position.

29. A bone anchor device for attaching connective tissue to bone, comprising:

a body having a longitudinal axis, a distal end, and a proximal end;

a surface on said body distal end which slopes inwardly toward said axis from a distal portion of said surface toward a proximal portion thereof;

a suture anchoring member which is movable axially toward and away from said sloping surface, between a proximal position and a distal position, said suture anchoring member having a distal end surface and opposing axial surfaces, said distal end and opposing axial surfaces all comprising suture receiving surfaces for contacting suture material wrapped thereabout; and a length of suture material disposed about said suture anchoring member, such that when said suture anchoring member is in said proximal position, said suture material is clamped between said suture anchoring member and body surface.

30. The bone anchor device as recited in claim 29, wherein said length of suture material is in physical contact with each of said distal end and opposing axial surfaces.

31. The bone anchor device as recited in claim 29, wherein one of said opposing axial surfaces is sloped so that a width of said suture anchoring member tapers from a distal end to a proximal end thereof.

32. The bone anchor device as recited in claim 31, wherein said sloped axial surface and said inwardly sloped body distal end surface together define a tapered distal lumen.

33. The bone anchor device as recited in claim 1, wherein said inner walls which define said lumen are not substantially radially expandable.

34. A bone anchor device for attaching connective tissue to bone, comprising:

an outer body;

a lumen extending axially through said outer body, said lumen being defined by inner walls and having a smaller cross-section in a proximal portion of said outer body than in a distal portion thereof, such that at least portions of said inner walls taper inwardly in a proximal direction;

a wedge member disposed in a distal end of said lumen, said wedge member having outer walls which taper inwardly in a proximal direction therealong, such that a proximal portion of said wedge member has a smaller cross-section than a distal portion of said wedge member, said wedge member being axially movable in said lumen distal end; and a lumen disposed axially in said wedge member, said wedge member lumen being disposed in a substantially same orientation as is disposed the outer body lumen.

35. A bone anchor device for attaching connective tissue to bone, comprising:

an outer body;

a lumen extending axially through said outer body, said lumen being defined by inner walls and having a smaller cross-section in a proximal portion of said outer body than in a distal portion thereof, such that at least portions of said inner walls taper inwardly in a proximal direction; and an elongated wedge member disposed in a distal end of said lumen, said wedge member having outer walls which taper inwardly in a proximal direction therealong, such that a proximal portion of said wedge member has a smaller cross-section than a distal portion of said wedge member, and a distal end having a curved surface, said wedge member further being axially movable in said lumen distal end.

36. A bone anchor device for attaching connective tissue to bone, comprising:

an outer body;

a lumen extending axially through said outer body, said lumen being defined by inner walls and having a smaller cross-section in a proximal portion of said outer body than in a distal portion thereof, such that at least portions of said inner walls taper inwardly in a proximal direction; and an elongated wedge member disposed in a distal end of said lumen, said wedge member having outer walls which taper inwardly in a proximal direction therealong, such that a proximal portion of said wedge member has a smaller cross-section than a distal portion of said wedge member, said wedge member being axially movable in said lumen distal end.

* * * * *

UNITED STATES PATENT AND TRADEMARK OFFICE
CERTIFICATE OF CORRECTION

PATENT NO. : 6,585,730 B1
DATED : July 1, 2003
INVENTOR(S) : Seth A. Foerster

It is certified that error appears in the above-identified patent and that said Letters Patent is hereby corrected as shown below:

<u>Column 8,</u>
Line 1, after "portion of" change "bon e" to -- bone --.

<u>Column 12,</u>
Line 55, change "suture;" to -- suture. --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,585,730 B1
DATED : July 1, 2003
INVENTOR(S) : Seth A. Foerster

It is certified that error appears in the above-identified patent and that said Letters Patent is hereby corrected as shown below:

Column 8,
Line 1, after "portion of" change "bon e" to -- bone --.

Column 10,
Line 6, paragraph was omitted. After "her hands." insert -- In operation, as the surgeon pulls on the free leg 32 of the suture 28, the bound leg 30 of the suture follows through the bone anchor until such time as the tissues binding in the bound leg 30 of the suture 28 creates a tension in the suture 28. At this point, tension in the suture 28 tends to urge the wedge body 20 up into the tapered distal lumen 18, pinching the suture 28 between the tapered distal lumen 18 and the tapered end 22 of the wedge body 20. As the tension in the bound leg 30 of the suture 28 increase, the force on the wedge body 20 increases. --

Column 12,
Line 55, change "suture;" to -- suture. --

Signed and Sealed this

Twenty-third Day of November, 2004

JON W. DUDAS
*Director of the United States Patent and Trademark Office*